United States Patent
Swanda et al.

(10) Patent No.: US 9,688,953 B2
(45) Date of Patent: Jun. 27, 2017

(54) SYSTEMS AND METHODS OF SEPARATING AND SINGULATING EMBRYOS

(71) Applicant: WEYERHAEUSER NR COMPANY, Federal Way, WA (US)

(72) Inventors: Anthony P. Swanda, Snoqualmie, WA (US); Henry M. Givens, Tacoma, WA (US)

(73) Assignee: Weyerhaeuser NR Company, Seattle, WA (US)

( * ) Notice: Subject to any disclaimer, the term of this patent is extended or adjusted under 35 U.S.C. 154(b) by 161 days.

(21) Appl. No.: 14/665,344

(22) Filed: Mar. 23, 2015

(65) Prior Publication Data

US 2015/0284672 A1 Oct. 8, 2015

Related U.S. Application Data

(60) Provisional application No. 61/974,206, filed on Apr. 2, 2014.

(51) Int. Cl.
*B07B 4/08* (2006.01)
*C12M 1/00* (2006.01)
*C12N 5/04* (2006.01)

(52) U.S. Cl.
CPC .............. *C12M 47/04* (2013.01); *B07B 4/08* (2013.01); *C12N 5/04* (2013.01)

(58) Field of Classification Search
CPC .... B03B 5/00; B03B 5/70; B07B 4/08; C12N 5/04; A01H 4/005; C12M 47/04
USPC ....................................................... 209/551
See application file for complete search history.

(56) References Cited

U.S. PATENT DOCUMENTS

| | | | | |
|---|---|---|---|---|
| 7,560,611 | B2 * | 7/2009 | Adams | A01H 4/001 800/278 |
| 7,665,243 | B2 * | 2/2010 | Nehra | A01H 4/001 435/283.1 |
| 7,685,767 | B2 * | 3/2010 | Timmis | A01H 1/04 47/57.6 |
| 7,785,884 | B2 * | 8/2010 | Grob | A01H 4/001 435/422 |
| 8,580,566 | B2 * | 11/2013 | Stout | A01H 4/001 435/420 |
| 8,925,245 | B2 * | 1/2015 | Brownell | C12N 5/04 47/58.1 R |
| 8,931,208 | B2 * | 1/2015 | Swanda | A01H 4/005 47/57.6 |
| 9,040,301 | B2 * | 5/2015 | Aidun | A01H 4/001 435/420 |
| 9,138,750 | B2 * | 9/2015 | Swanda | B03B 5/00 |
| 9,527,115 | B2 * | 12/2016 | LaRose | B07C 5/342 |
| 2007/0099293 | A1 * | 5/2007 | Gupta | A01H 4/001 435/289.1 |

(Continued)

*Primary Examiner* — Joseph C Rodriguez
(74) *Attorney, Agent, or Firm* — Perkins Coie LLP

(57) ABSTRACT

Separating and singulating embryos employs a spray module configured to spray a plurality of embryos which are loaded on a porous substrate so as to separate and singulate the plurality of embryos, and a drying module configured to dry the plurality of separated and singulated embryos retained on the porous substrate while the porous substrate is moved across the drying module. A robotic arm operates to transfer the porous substrate from module to module, and a control device controls the operation of the system of separating and singulating embryos.

28 Claims, 9 Drawing Sheets

(56) References Cited

U.S. PATENT DOCUMENTS

2008/0015790 A1\* 1/2008 Timmis ................... A01H 1/04
　　　　　　　　　　　　　　　　　　　　　　702/19
2011/0076715 A1\* 3/2011 Swanda ................... A01H 4/00
　　　　　　　　　　　　　　　　　　　　　　435/34

\* cited by examiner

```
                    ┌──────────────┐
                    │  Dispensing  │ — 100
                    └──────┬───────┘
                           ▼
                    ┌──────────────┐
                    │   Loading    │ — 200
                    └──────┬───────┘
                           ▼
                    ┌──────────────┐
                    │    Spray     │ — 300
                    └──────┬───────┘
                           ▼
                    ┌──────────────┐
                    │    Drying    │ — 400
                    └──────┬───────┘
                           ▼
                    ┌──────────────────┐
                    │ Bioreactor Loading│ — 500
                    └──────────────────┘
```

FIG. 1

SYSTEMS AND METHODS OF SEPARATING AND SINGULATING EMBRYOS

CROSS-REFERENCE TO RELATED APPLICATION

This application is entitled to and claims the benefit of priority under 35 U.S.C. §119 from U.S. Provisional Patent Application Ser. No. 61/974,206 filed Apr. 2, 2014, and titled SYSTEMS AND METHODS OF SEPARATING AND SINGULATING EMBRYOS, the contents of which are incorporated herein by reference.

BACKGROUND

Modern silviculture often requires the planting of large numbers of genetically identical plants that have been selected to have advantageous properties. Production of new plants by sexual reproduction, which yields botanic seeds, is usually not feasible. Asexual propagation, via the culturing of somatic or zygotic embryos, has been shown for some species to yield large numbers of genetically identical embryos, each having the capacity to develop into a normal plant.

Somatic cloning is the process of creating genetically identical plants from plant somatic tissue. Plant somatic tissue is plant tissue other than the male and female gametes. In one approach to somatic cloning, plant somatic tissue is cultured in an initiation medium which includes hormones, such as auxins and/or cytokinins that initiate formation of embryogenic cells that are capable of developing into somatic embryos. The embryogenic cells are then further cultured in a maintenance medium that promotes multiplication of the embryogenic cells to form pre-cotyledonary embryos (i.e., embryos that do not possess cotyledons). The multiplied embryogenic cells are then cultured in a development medium that promotes development of cotyledonary somatic embryos.

At the end of development phase, the embryos may be present in a number of stages of maturity and development, and are typically attached to or imbedded in embryogenic suspensor mass (ESM). Separation and singulation are processing steps that typically occur at the end of development and maturation in which plant embryos are physically separated from each other and the underlying ESM before further processing, such as placement onto germination or pre-germination medium for further treatment prior to insertion into manufactured seeds.

SUMMARY

The present disclosure is directed to providing systems and methods of separating and singulating embryos for research purposes.

A system of separating and singulating embryos comprises a spray module configured to spray a plurality of embryos loaded on a porous substrate so as to separate and singulate the plurality of embryos, a drying module configured to dry the porous substrate upon which the plurality of separated and singulated embryos are retained, and a robotic arm operable of transferring the porous substrate from module to module in a predetermined sequence. The system of separating and singulating embryos further comprises a loading module, a dispensing module configured to dispense a blank porous substrate mounted in a frame which is transferred to a predetermined loading position at the loading module for loading embryos, and a bioreactor loading module for loading the porous substrate upon which the plurality of separated and singulated embryos are retained into a bioreactor, and a control device controlling the dispensing module, the spray module, the drying module, the conditioning module, and the robotic arm.

A method of separating and singulating embryos comprises the steps of spraying a plurality of embryos which are loaded on a porous substrate so as to separate and singulate the plurality of embryos at a spray module, drying the porous substrate upon which the plurality of separated and singulated embryos are retained, and transferring the porous substrate from module to module in a predetermined sequence by a robotic arm. The method of separating and singulating embryos further comprises the steps of dispensing a blank porous substrate from a dispensing module, loading a plurality of embryos onto the blank porous substrate while it is transferred to a predetermined loading position, loading the porous substrate upon which the plurality of separated and singulated embryos are retained into a bioreactor at a bioreactor loading module, and controlling the dispensing module, the spray module, the drying module, the bioreactor loading module, and the robotic arm by a control device.

BRIEF DESCRIPTION OF THE DRAWINGS

The following detailed description may be better understood when read in conjunction with the appended drawings. For the purposes of illustration, various examples of aspects of the disclosure are shown in the drawings; however, the invention is not limited to the specific methods and instrumentalities disclosed.

FIG. 1 is a flow diagram illustrating the process of separating and singulating embryos utilizing a separation and singulation for research (SSR) system according to one embodiment;

DETAILED DESCRIPTION OF ILLUSTRATIVE EMBODIMENTS

Figure 2:
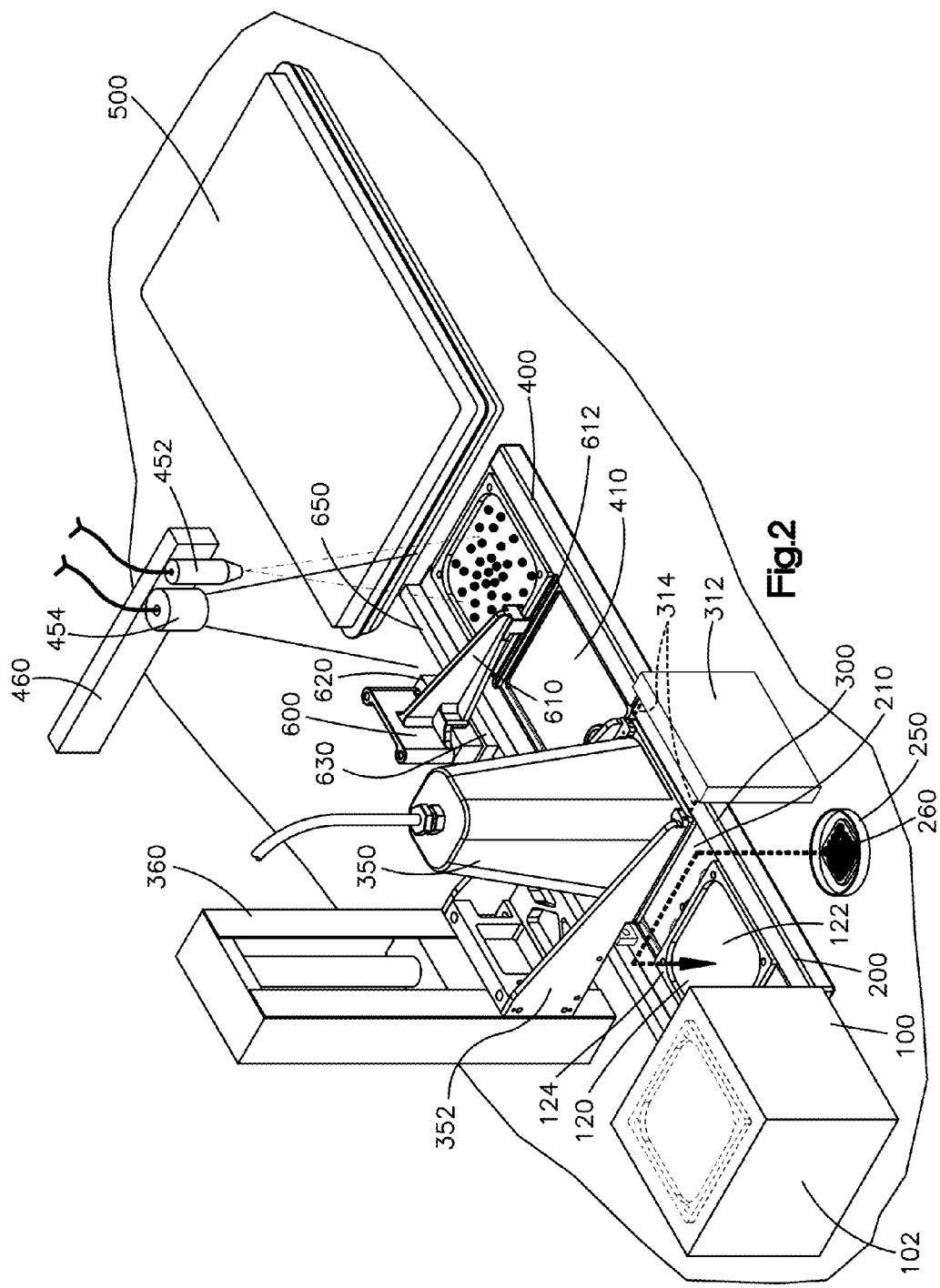
FIG. 2 is a perspective view of a SSR system according to one embodiment.

As used herein, the term "embryogenic suspensor mass" (ESM) refers to early stage embryos in the process of multiplication by budding and cleavage.

As used herein, the term "embryogenic tissue" refers to an aggregate of tens to hundreds of embryogenic cells that form embryogenic suspensor mass.

As used herein, the term "plant embryo" refers to a somatic plant embryo. Somatic plant embryos may be produced by culturing embryogenic tissue by standard methods under laboratory conditions in which the cells comprising the tissue are separated from one another and urged to develop into minute complete embryos. As used herein, "plant embryo" includes embryos at various stages of development.

As used herein, the terms "cotyledonary embryo" refers to an embryo that possesses one or more cotyledons. Cotyledonary embryos have a well-defined elongated bipolar structure with latent meristem with cotyledonary primordial at one end and a potential radicle at the opposite end. The cotyledonary structure frequently appears as a small "crown" at one end of the embryo.

As used herein, the terms "separate", "separation" refer to the process of separating mature embryos from attached ESM and immature embryos.

As used herein, the terms "singulate", "singulation" refer to the process of acquiring individual, discrete embryos.

As used herein, the term "SSR" refers to the processes of the separation and singulation.

As used herein, the term "module" refers to a processing area or station.

As used herein, the term "COW" refers to the process of conditioning over water.

As used herein, the term "normal singulation" refers to the process of separating and singulating developed embryos contained in cultures after the Development and Stratification (a cold, late maturation treatment) processes.

As used herein, the term "early singulation" refers to the process of separating and singulating immature embryos part way through Development (majority embryos present are immature).

The somatic embryogenesis process is a process to develop plant embryos in vitro. Methods for producing plant somatic embryos are known in the art and have been previously described. Generally, the somatic embryogenesis process includes the steps of: (1) initiation or induction, to initiate formation of embryogenic tissue, such as embryogenic suspensor mass (ESM), which is a white mucilaginous mass that includes early stage embryos having a long, thin-walled suspensor associated with a small head with dense cytoplasm and large nuclei; (2) multiplication, sometimes referred to as maintenance, to multiply and mass produce embryogenic tissue; (3) development, to develop and form mature cotyledonary somatic embryos; and (4) post development steps such as separation, singulation, stratification, germination, growing into plants, such as through placement into manufactured seeds.

At the end of the development period, the embryos are to various degrees attached to and embedded in suspensor tissues and residual underdeveloped ESM, together with incompletely developed embryos, abnormally formed embryos, undersized or oversized embryos, and other pieces of non-embryo plant material, and to other embryos. It is important for subsequent normal germination to separate the embryos from the suspensor mass and from other embryos and to singulate the embryos into individual, discrete embryos.

The present application is directed to a system and method for separating and singulating embryos (referred to herein as the SSR system and method). The SSR system and method are designed to process a large number of small units of culture, e.g., culture on Petri plates. Thus, the SSR system and method are well suited for research focused activities such as genotype screening, e.g., as part of a clonal field test, and for research experiments where a high degree of replication on a small scale (e.g., a large number of Petri plates) are required.

Figure 3:
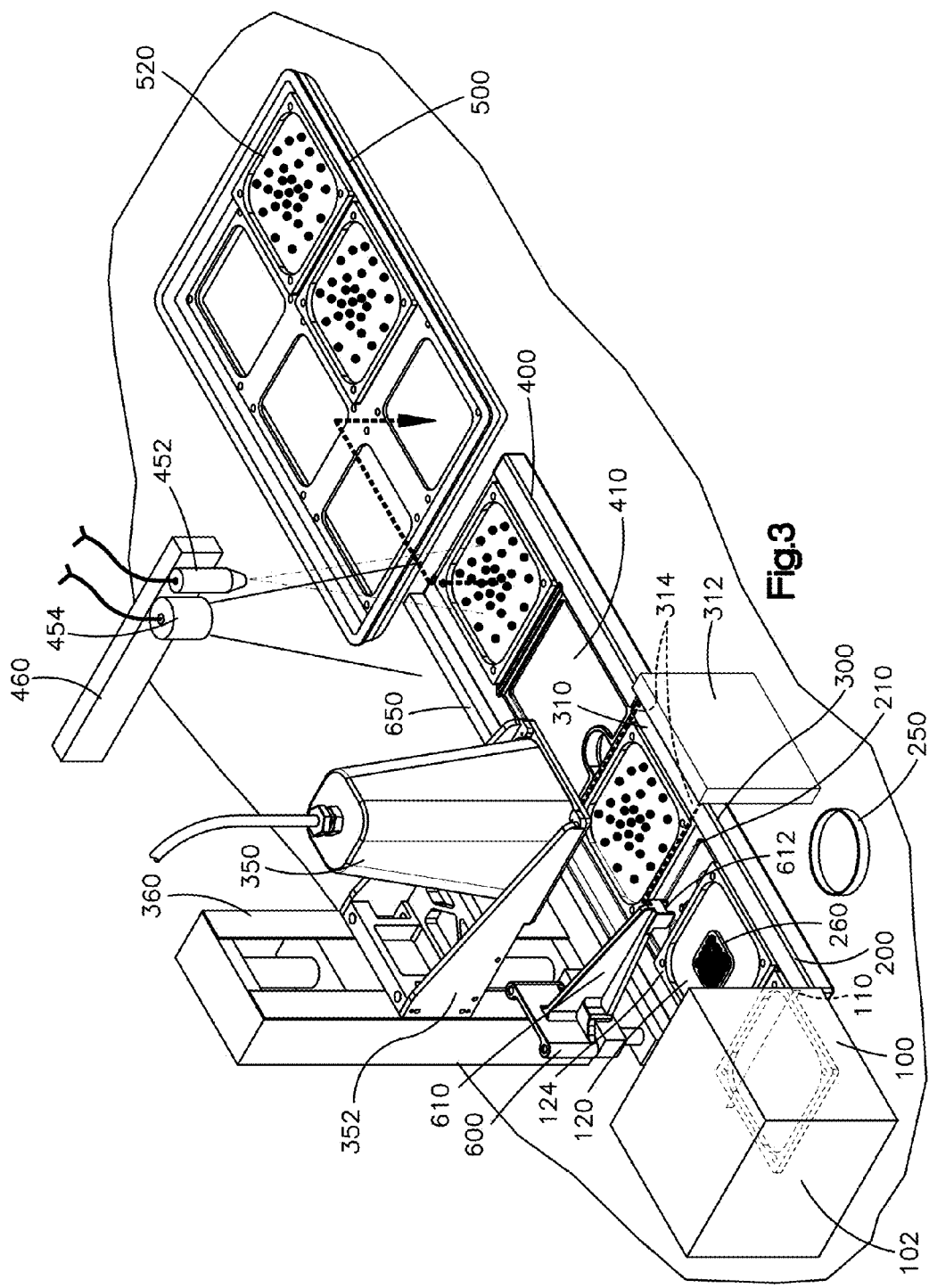
FIG. 3 is another perspective view of a SSR system according to one embodiment.

As shown in FIG. 1, one embodiment of the separation and singulation system (referred to as the SSR system) 10 comprises five major stations or modules: (1) dispensing 100; (2) loading 200; (3) spray 300; (4) drying 400; and (5) bioreactor loading 500. Blank s-frames or s-frames with disposed embryos may be transferred from module to module by use of a robotic arm 600 (as shown in FIGS. 2 and 3). At the same time, there may be a need of manually transferring the s-frames with disposed embryos from the drying module 400 to the bioreactor loading module 500. The dispensing module 100, the loading module 200, the spray module 300, the drying module 400, the bioreactor loading module 500, and the robotic arm 600 are contained in a sterile enclosure. The dispensing module 100, the loading module 200, the spray module 300, and the drying module 400 may be arranged consecutively in a line from left to right, or vice versa. The SSR system 10 may implement an automated process of separating, singulating embryos disposed on the s-frames in a single spray step.

As shown in FIGS. 2 and 3, the loading module 200, the spray module 300, and the drying module 400 may include a loading platform 210, a spray platform 310, and a drying platform 410 which is divided into two sections, respectively. The loading platform 310, the spray platform 310, and the drying platform 410 may be installed on a support frame (not shown) which is fixed on an operation table (not shown). A dispensing slit 110 of the dispensing module 100, the platforms 210, 310, and 410 may be located at the same height above the operation table by fixing on the support frame. In this way, the s-frames can flow from one end to another end of the processing line of the SSR system. The dispensing module 100, the platforms 210, 310, and 410 may be designed to easily remove, insert, and/or sterilize.

The platforms 210, 310, 410 may be one integrated platform or separate ones. In some embodiments, the loading platform 210 and the spray platform 310 may be formed as one integrated platform with two sections; the drying platform 410 may be a separate one which is divided into two sections. As shown in FIGS. 2 and 3, the modules 100, 200, 300, and 400 are arranged from left to right, which allows the s-frames dispensed from the module 100 to flow from left to right on the platform 210, 310, and 410. In another embodiment, they can be arranged from right to left, whereby the s-frames flow from right to left.

In a further embodiment, two processing lines, a left line and a right line, may be built on the operation table. The handedness of the left line and the right line may be arranged opposite of each other. In the left line, the dispensing module 100, the loading module 200, the spray module 300, the drying 400, and the bioreactor loading module 500 may be arranged consecutively in a line from left to right, whereby s-frames flow from left to right. In the right line, the modules 100, 200, 300, 400, and 500 may be arranged in a line from right to left, whereby s-frames flow from right to left. The left and right processing lines flow towards each other so that one operator can load dried s-frames into either of two conditioning containers in the left line and the right line from one operating position. Another advantage of arranging two processing lines is that the operator may prefer one handedness over the other. Furthermore, the operator may switch back and forth between the two processing lines so as to relieve ergonomic strain.

The dispensing module 100 is a first module of the SSR system. The s-frame module 100 is used to eject blank s-frames. As shown in FIGS. 2 and 3, the dispensing module 100 includes an s-frame canister 102. The s-frame canister 102 may be configured to contain a stack of blank s-frames. The s-frame canister 102 includes the dispensing slit 110 positioned at the bottom of one side facing the processing line. The dispensing slit 110 may be configured to easily release an s-frame from the s-frame canister 102. The s-frame canister 102 may be installed in such a way that the dispensing slit 110 is located at the same height as the platforms 210, 310, and 410 above the operation table and is immediately next to one end of the loading platform 210. An ejecting mechanism (not shown) for ejecting blank s-frames may be provided in the dispensing module 100. By starting the processing line of the SSR system, a blank s-frame will be partially ejected from the dispensing slit 110 to the loading platform 210. Then, the robotic arm 600 can move the blank s-frame to a predetermined position for loading culture containing embryos.

As shown in FIGS. 2 and 3, an s-frame 120 includes a porous substrate 122 and a frame 124. The porous substrate 122 may be mounted in the frame 124. The porous substrate 122 includes a top surface and a bottom surface. The top surface of the porous substrate 122 may be used to receive a culture containing embryos. The porous substrate 122 may be any desired shape and dimension. While the porous substrate 122 as shown in FIGS. 2 and 3 is rectangular, it can be any other desired shape, such as square shape. Exemplary dimensions may be from a surface area of about 10 square inches to 30 square inches or greater, such as 40 or 50 square inches. The fabric material of the porous substrate 122 should not be hydrophobic because it may lead to water pooling on the top surface of the porous substrate 122 while in the spray process at the spray module 300. The fabric material must also be able to survive multiple autoclaving (15 psig steam—251 F). Examples of suitable material for the porous substrate 122 include polyester, polyamide, nylon, and so on. While fully developed embryos have typically been processed, various trials have shown that it is possible to process embryos at an earlier stage, thereby improving embryo quality. By way of example and without limitation, Saatifil Monofilament Polyester PES 810/55 may be used for normal singulation; Saatifil Monofilament Polyester PES 700/68 may be used for early singulation. For the purpose of imaging embryos which requires good color contrast between embryos and the porous substrates, the fabric material for making the porous substrate 122 may be preferably selected to have black or any other color which contrasts highly with the color of the embryos.

The porous substrate of an s-frame has a plurality of pores. The diameters of the pores may be referred to the opening width. The selection of opening width is generally related to dependent on the size of the embryos that users want to capture. Opening sizes between 425 microns and 2000 microns have been tried for loblolly pine and Douglas Fir embryos. By way of example and without limitation, the porous substrate may have an opening width in the range of from about 500 microns to about 2000 microns, such as about 810 micron for normal singulation and about 700 micron for early singulation.

The ratio of open area formed by all pores to the total area of the porous substrate may be referred to as open area percentage. The open area percentage may affect how easily water passes through the porous substrate when it is in the spray process at the spray module 300. The opening width may also affect it too. When the open area percentage is below 50%, water may start to pool on the porous substrate in the spray process. The pooled water tends to float embryos out to the edges of the s-frame and tends to aggregate them. By way of example and without limitation, the open area percentage may be equal to or higher than 50%, preferably equal to or higher than 55%. By way of example and without limitation, the open area percentage of porous substrates with 810 micron opening width may be 55%; the open area percentage of porous substrates with 700 micron opening width may be 68.

As mentioned above, a blank s-frame can be ejected from the dispensing slit 110 of the s-frame dispensing module 100. Then, the robotic arm 600 can move the blank s-frame to a predetermined position of the loading module 200. When the s-frame 120 is moved to the predetermined position of the loading module 200 as shown in FIGS. 2 and 3, an operator may manually load a culture containing embryos from a Petri plate 250 to the approximate center of the s-frame 120. By way of example and without limitation, the culture can be transferred from the single Petri plate 250 to the s-frame 120 by using a 2 inch×2 inch square mesh 260 on which the culture is originally plated. Typically, the culture does not fully cover the square mesh 260. Thus, preferably less than 4 square inches of culture may be loaded to the s-frame 120.

Figure 4:
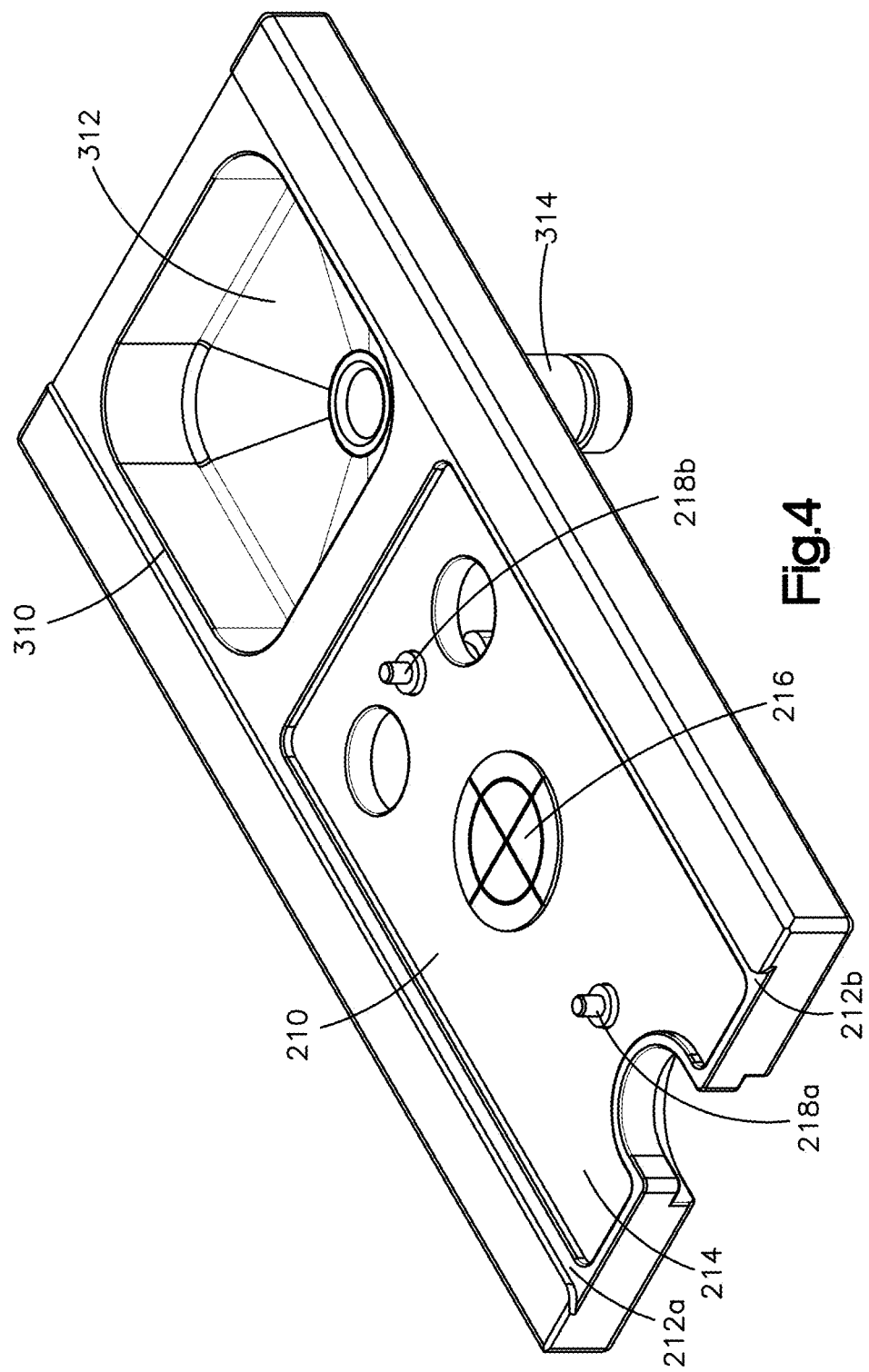
FIG. 4 illustrates a perspective view of a loading platform and a spraying platform according to one embodiment.

FIG. 4 illustrates an embodiment of the loading platform 210 which is formed as one integrated platform with the spray platform 310. A pair of steps 212a and 212b may be formed longitudinally adjacent to the two opposite sides of the platform 210, 310, and 510 respectively. The steps 212a and 212b may be used to support the two longitudinal sides of the frame of an s-frame so that the s-frame can be smoothly longitudinally moved by the robotic arm 600 from module to module. A rectangular recess 214 may be formed on the top surface of the loading platform 210. A loading target 216 may be provided at the approximate center of the loading platform 210. The loading target 216 may be used to show an operator a predetermined position for loading a culture. A pair of movable pins 218a and 218b may be formed symmetrically at the two sides of the loading target 216. The pair of pins 218a and 218b may move up and down. When the robotic arm 600 moves an s-frame to and from the loading module 200, the pins 218a and 218b may move down. When the s-frame 120 is moved to the predetermined loading position, the pins 218a and 218b may move up so as to capture the s-frame, whereby the operator cannot accidently move the s-frame while loading the culture from the square mesh 260 in the Petri plate 250 onto the s-frame 120.

As shown in FIG. 4, a sink 312 may be formed in the spray platform 310. The sink 312 may be connected to a drain 314. The sink 312 and the drain 314 may be used for removing liquid and waste, such as embryogenic suspensor mass removed from the embryos, and embryos of undesired size, resulting from the separation and singulation process.

Figure 5:
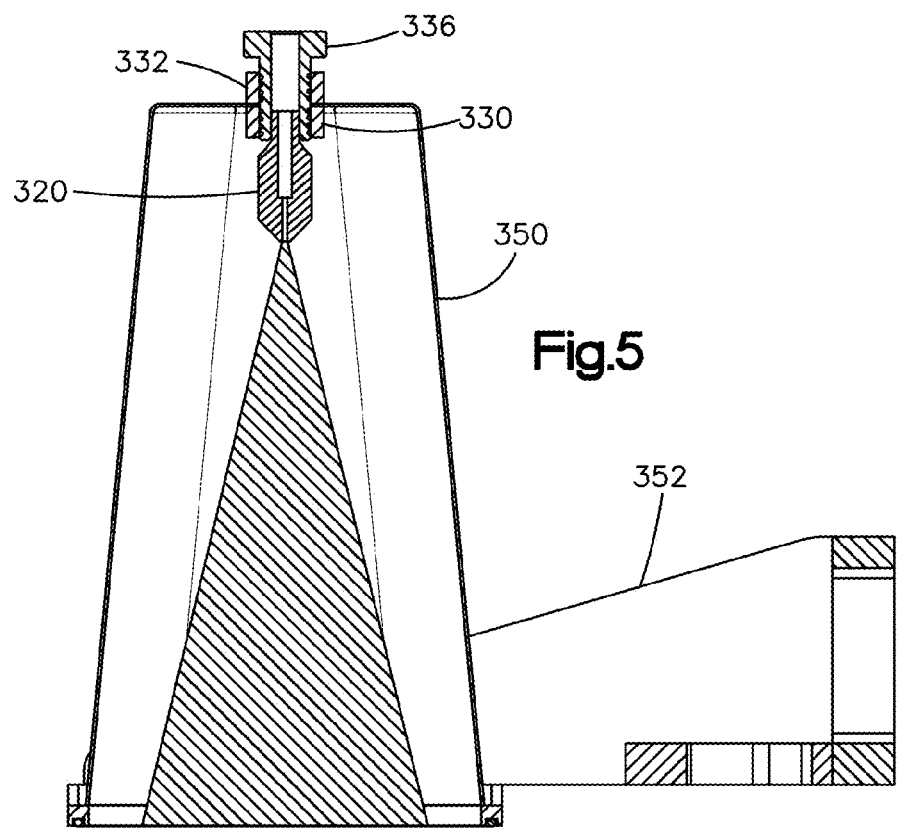
FIG. 5 is a longitudinal section view of a spray hood with a spray nozzle mounted to the spray hood in accordance with one embodiment.

As shown in FIG. 5, the spray module 300 further comprises a spray nozzle 320 and a spray hood 350. The spray nozzle 320 may be mounted to the approximate center of the internal top surface of the spray hood 350 by a first nut 330 and a second nut 332. The height of the spray nozzle 320 relative to the spraying platform 310 may be adjusted by rotating a rotatable member 336. The selection of the spray nozzle 320 may depend on the size, shape, and pressure of a desired spray. By way of example and without limitation, the spray nozzle 320 may be a narrow angle spray, such as 1/8GG-3007 FullJet Nozzle manufactured by Spraying System Co. The spay hood 350 may surround the spray nozzle 320 and the liquid spray produced by the nozzle 320.

The spray hood 350 may be movably connected to a lift mechanism 360 (as shown in FIGS. 2 and 3) by a mounting frame 352. The spray hood 350 and the mounting frame 352 may be designed to easily remove, insert, and/or sterilize. The lift mechanism 360 may raise and lower the spray hood 350 to engage the s-frame located at the predetermined spray position. The lift mechanism 360 may also raise the spray hood 350 to such a height that the robotic arm 600 can freely move below the spray hood 350. The lift mechanism 360 may be of various constructions, such as using linear actuators. The spray hood 350 may be of a shape and size such that it engages around the frame of an s-frame at the predetermined spray position to form a seal, thus creating an isolated spray system. The isolated system contains the aerosols generated from the liquid spray emanating from the spray nozzle 320, thereby reducing the possible spread of any contamination that may be present in the spray aerosols.

As shown in FIGS. 2 and 3, a pair of beam detectors 312 (one as a transmitter and another as a receiver) may be provided closely against the two opposite longitudinal sides of the spray platform 310. The beam detectors 312 may be positioned in such way that a pair of beams 314 produced by the beam detector 312 are above and a certain distance away from the spray platform 310. The beams 314 may be used for locating the s-frame under the spray hood 350. The beam detectors 312 may be any suitable ones, such as laser beam detectors and infrared beam detectors. There may be proximity sensors (not shown) mounted on the lift mechanism 360. The proximity sensors may determine when the spray hood is fully lowered or fully raised. When the spray hood 350 is fully lowered by the lift mechanism 360 to engage over the s-frame located at the predetermined spray position, the spray can be started.

The standard spray liquid is water; however, water with added osmotic agent, such as sugar or sugar alcohol, may be beneficial for early stage embryos. The spray nozzle 320 may produce a uniform, round, full spray pattern with medium to large sized drops (not atomized). By way of example and without limitation, the spray pressure at the spray nozzle 320 may range from 20 to 50 psi, preferably approximately 30 psi. If the spray pressure at the spray nozzle 420 is below 20 psi, the spray nozzle 420 may not develop a uniform spray pattern and may have "holes" in it.

The spray produced by the spray nozzle 320 may provide a downward force on the embryos disposed on the s-frame located at the spraying position. The downward force may push waste, such as suspensor tissues, residual underdeveloped ESM, and embryos of undesired size, through the pores of the porous substrate at the spraying position so as to separate desired embryos from the underlying suspensor mass and undersized embryos. Meanwhile, the downward force may, to some degree, singulate the embryos retained on the s-frame. The spray produced by the spray nozzle 320 may provide a tangential force on the plant embryos disposed on the s-frame. The tangential force may roll embryos out towards the edges of the s-frame and may cause the plant embryos to wiggle on the s-frame. The tangential force may, to some extent, singulate embryos separated by the downward force from ESM and undesired embryos by the downward force. However, the tangential force needs to be limited so that it will not have adverse effect on the separation process implemented by the downward force.

The downward force may be changed by various spray pressure. By the way of example, the spray pressure range of 20-50 psi may result in a downward force ranging from 0.0083 to 0.01441 lbs per in$^2$. In addition to the spray pressure, the downward force may also be affected by other factors, such as nozzle type and spray distance. The downward force may be as high as 0.022 lbs per in$^2$ without damaging embryos. By the way of example, the downward force may be approximately 0.011 lbs per in$^2$. The required downward force for separating embryos depends on ESM properties because ESM is a gel-like mat that has embryos embedded in it. Embryo development stage and culture temperature may affect how gelled ESM is. The downward force being approximately 0.022 lbs per in$^2$ works well for the majority of cultures following development and stratification (i.e., what it is referred above as "normal singulation"). A downward force being significantly less than 0.011 lbs per in$^2$ would be required for early singulation because the ESM mat is softer and less gelled at an early stage.

Spray time required for separation depends on the toughness of the ESM. Typically, tougher ESM need longer spray time. By the way of example without limitation, the spray time may range from 2 to 30 second, such as 20 seconds for normal separation and 4 seconds for early separation. The spray time may be up to a minute for very tough ESM which tends to result when cultures are stored for extended periods in stratification (a cold treatment).

Figure 6:
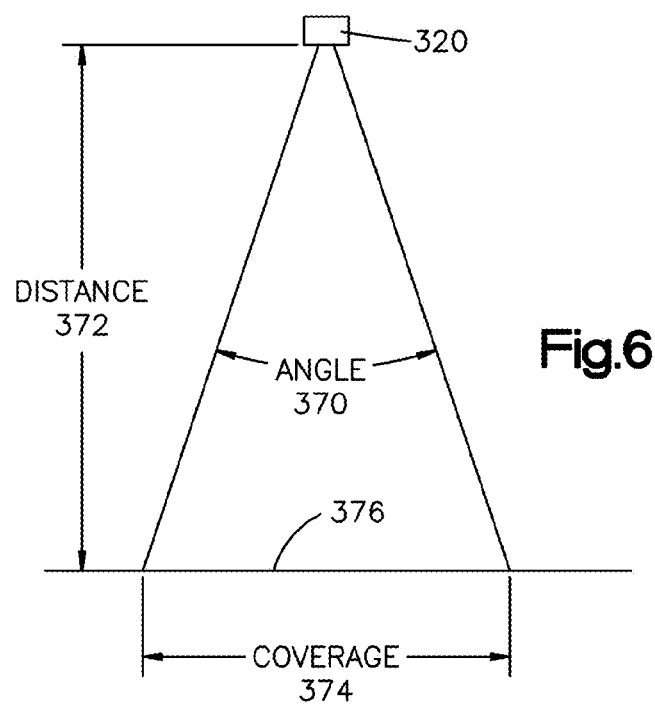
FIG. 6 is a schematic diagram of liquid spray produced by a spray nozzle.

FIG. 6 is a cross section view of a full cone spray pattern. As shown in the figure, the top angle between two sides is referred to as spray angle 370. The distance between the spray nozzle 320 and the surface of the s-frame at the spray position is referred to as spray distance 372. The area covered by the spray produced by the spray nozzle 320 is referred to as coverage area. A theoretical coverage area 376 is shown in FIG. 6. A practical coverage area (not known) may diverge from the theoretical coverage area 376.

By way of example and without limitation, the spray angle 370 may range from about 25 degrees to about 35 degrees, such as from about 26 degrees to about 32 degrees. Higher spray angles might be problematic because higher spray angles may lead to strong tangential force so that the tangential force rolls embryos out to the edges of the s-frame faster than a speed that the downward force pushes the ESM or undesired embryos through the s-frame. In that case, the embryos cannot be separated from the underlying suspensor mass and undersized embryos. A more narrow spray angle may be acceptable; however, in that case an increased spray distance may be needed to achieve the same coverage area.

As shown in FIG. 6, since the spray fans outward from the spray nozzle 320, increasing the spray distance 372 may increase the coverage area 376. At the same time, increasing the spray distance 372 may reduce downward impact force per unit area because of the increase of the coverage area while the amount of impacting water droplets remains the same. As mentioned above, the height of the spray nozzle 320 may be adjustable, which enables the spray nozzle 320 to be mechanically raised or lowered relative to the top of the spray hood 350. This arrangement allows the users to adjust the spray distance 372 without fabricating a new spray hood and spray nozzle. The spray distance 372 (for a given spray angle) is a function of the desired spray coverage area and the downward impact force. By way of example and without limitation, if the spray distance is selected as being 7.25 inches, it will produce a spray pattern with a diameter of 3.5 inches at the s-frame surface. A desired spray coverage area resulting from the selection of spray distance may leave a certain size of outer area on the s-frame where little water is impacting the porous substrate of the s-frame. The unsprayed outer area of the s-frame may be useful for draining water and leaving an area for embryos to collect so that they are not up against the frame of the s-frame. By way of example and without limitation, the unsprayed outer area may range from 0.7 inch to 1.5 inch wide perimeter, such as ⅔ inch.

Figure 7:
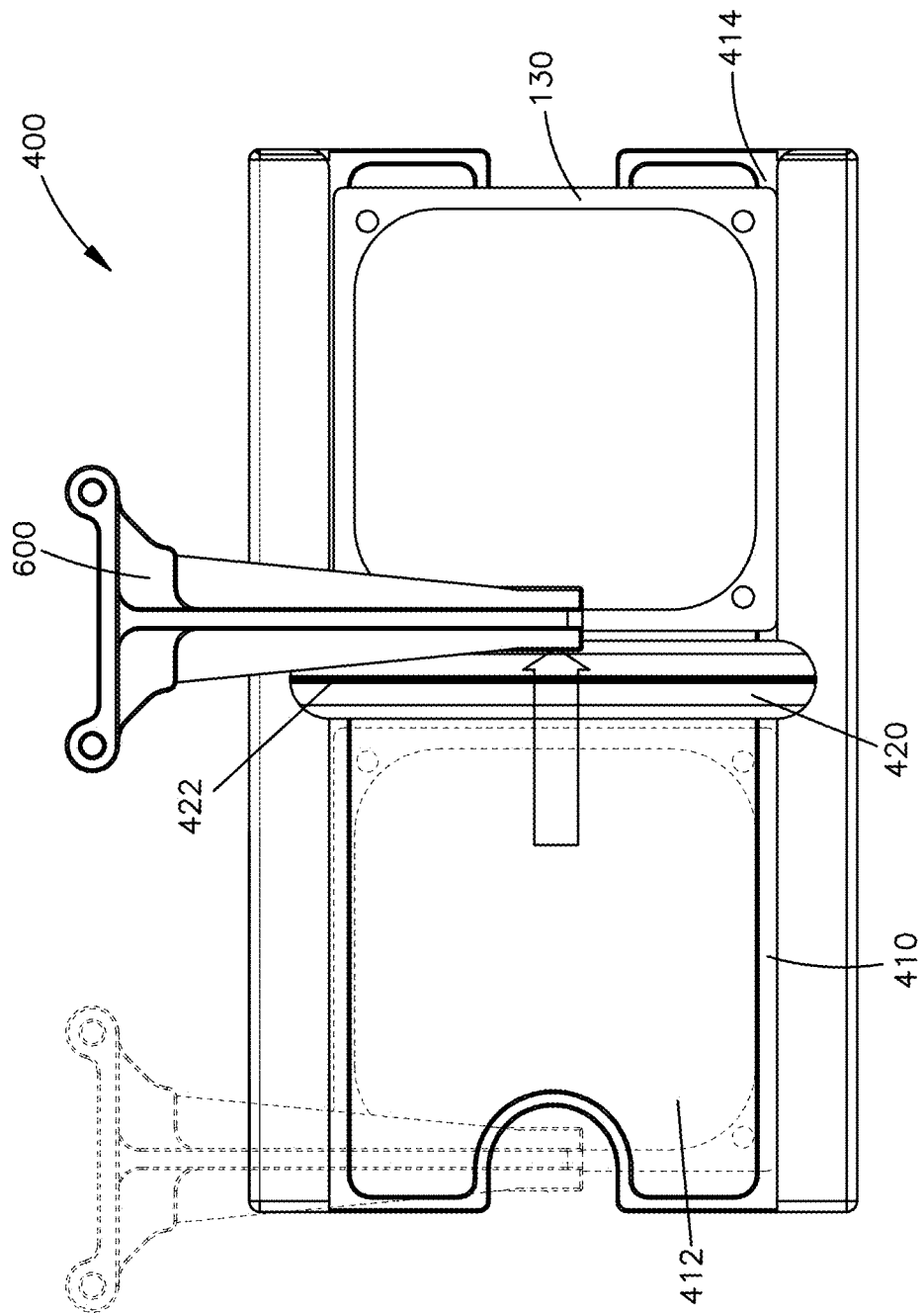
FIG. 7 illustrates a top planar view of a drying module in accordance with one embodiment.

After separating and singulating at the spray module 300, an s-frame 130 with embryos may be transferred by the robotic arm 600 to the drying module 400. The drying module 400 is used to remove excess water or other spray liquid from the s-frame 130 upon which the separated and singulated embryos are deposited. A variety of methods may be used to remove the water or other spray liquid from the s-frame 130. As shown in FIG. 7, one embodiment of the drying module 400 includes the drying platform 410 divided into two sections 412 and 414, a vacuum housing 420 which is located between the two sections of the drying platform 410, a narrow elongated opening 422 which is provided on the vacuum housing 420. The elongated opening 422 is in communication with a vacuum source (not shown). The elongated opening 422 may be configured to ensure that the vacuum can be even across the length of the elongated opening 422. Typically, the width of the elongated opening 422 may range from about 0.001 inches to 1.0 inch or greater, such as from 0.001 inches to about 0.1 inches, such as from 0.04 inches to 0.06 inches, such as about 0.02 inches. Other widths of the opening 422 may be suitable, depending on the dimensions of the s-frame.

During operation, the s-frame 130 may be transferred to the first section 412 of the drying platform 410. The robotic arm 600 may move the s-frame across the opening 422 of the vacuum housing 420 to the second section 414 of the drying platform 410. As the s-frame 130 is moved across the opening 422, the bottom surface of the s-frame 130 is in contact with the opening 422, which is in communication with the vacuum source, resulting in water or other spray liquid being removed from the s-frame 130 and air being drawn over and around the embryos disposed on the top surface of the s-frame 130 and through the s-frame 130.

In some embodiments, the negative pressure generated by the vacuum source may range from about −0.5 psi to about 15 psi, such as from about −5 psi to about −12 psi. By the way of example without limitation, in one embodiment, the negative pressure is about −4.35 psi; the flow rate is about 170 liters per minute of air. In some embodiments, the negative pressure generated by the vacuum source may be constant as the elongated opening 422 is in communication with the vacuum source. In other embodiments, the negative pressure generated by the vacuum source may vary as the elongated opening 422 is in communication with the vacuum source.

In some embodiments, the s-frame 130 and the elongated opening 422 may move relative to each other at a speed in the range from about 1 millimeter per second to about 45 millimeters per second, preferably from about 1 millimeter per second to about 10 millimeters per second. In one embodiment, the s-frame 130 and the elongated opening 422 may move relative to each other at a speed of about 4 millimeters per second. By setting a certain speed of an s-frame with a given size relative to the elongated opening 422, the s-frame drying time may be determined. For instance, when the inside width of the s-frame is about 4.72 inch and the speed of the s-frame relative to the elongated opening 422 is 4 millimeters per second, the s-frame drying time is about 30 seconds.

In one embodiment, the vacuum housing 420 with the elongated opening 422 is rectangular in shape (e.g., bar-shaped) and is sized, depending on the size of the porous substrate of the s-frame, such that the vacuum housing 420 with elongated opening 422 will be in contact with substantially all of an area of a cross section of the porous substrate, but preferably will not be in contact with the entire area of the porous substrate at any one time. In one embodiment, the vacuum housing 420 with the elongated opening 422 is sized and shaped such that the vacuum housing 420 with the elongated opening 422 in use will be in contact with less than 1% of the entire area of the porous substrate of the s-frame at any one time, such as from about 0.01% to about 0.1%, such as about 0.02% to about 0.05%, such as about 0.04%.

Figure 8:
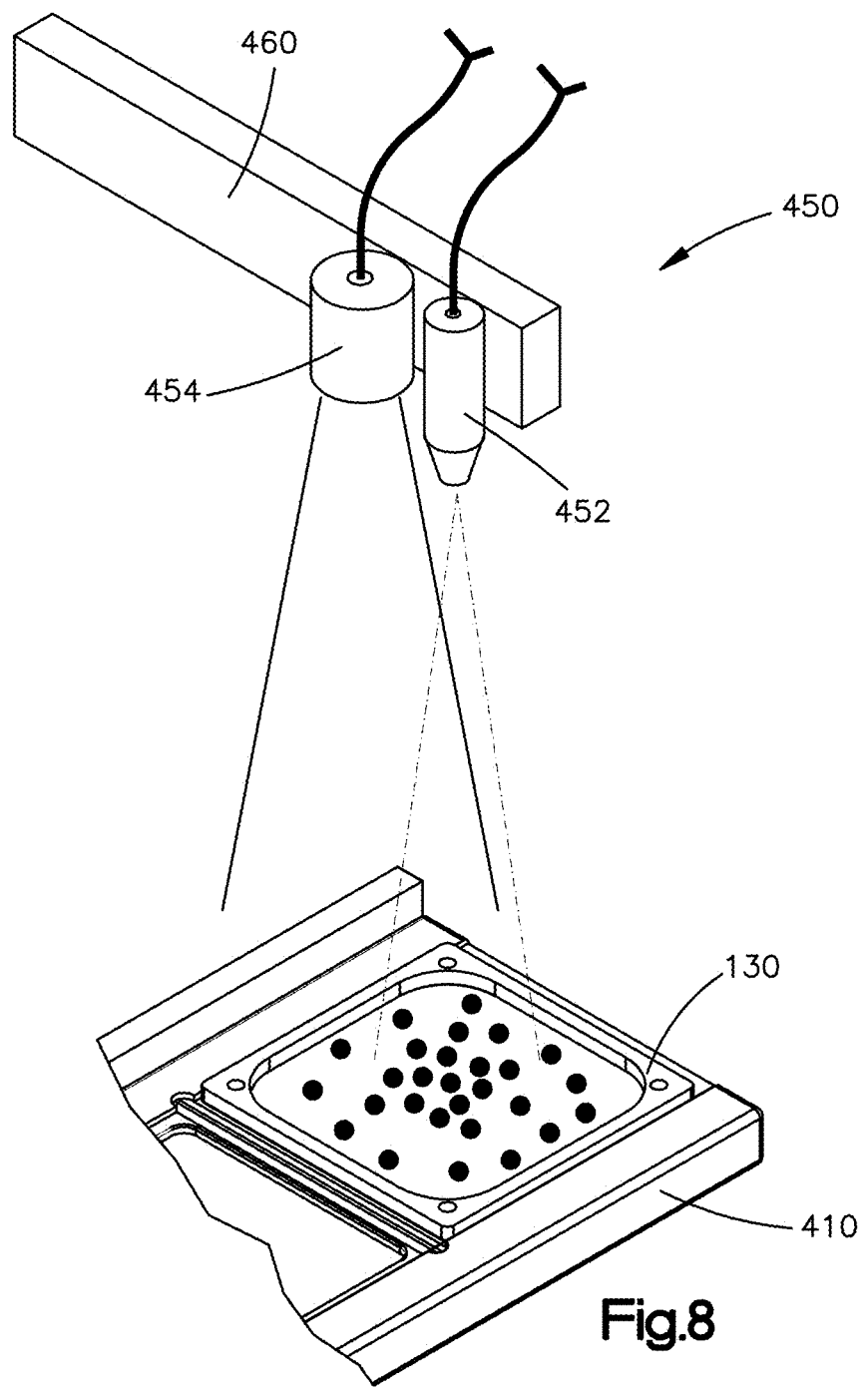
FIG. 8 illustrates a perspective view of a vision system in accordance with one embodiment.

FIG. 8 illustrates an overhead vision mechanism 450 in accordance with one embodiment. The overhead vision mechanism 450 can be used to count or at least estimate the number of embryos retained on the s-frame 130 after the separation and singulation process. The overhead vision mechanism 450 may be centered over the s-frame 130 after it has been dried and positioned on the second section 414 of the drying platform 410. The location may be referred to the dry end of the drying module. As shown in the FIG. 8, the overhead vision mechanism 450 comprises an image generator 452 and a light source 454. Both the image generator 452 and the light source 454 may be mounted in an arm 460. The image generator 452 may be positioned to generate an image of embryos retained on the dried s-frame 130. The light source 454 may be positioned to illuminate the dried s-frame 130 with separated and singulated embryos. The image generator 452 and the light source 454 may be mounted to face the dried s-frame 130 at approximately a right angle. The light source 454 may be positioned such that a beam of light produced by the light source 454 is approximately centered about the center of the dried s-frame 130. Any of a variety of image generators 452 and light sources 454 may be used. By way of example and without limitation, the image generator 452 may be a high resolution camera.

After drying at the drying module 400, the s-frame with separated and singulated embryos may be manually transferred to the fifth module of the SSR system, referred to herein as the "bioreactor loading module" 500. The bioreactor loading module 500 may be used for loading the s-frame upon which the separated and singulated embryos are retained into a bioreactor where further bioprocessing may occur. The further bioprocessing may be further development, maturation, or conditioning depending on the stage of embryos. The further bioprocessing may also depend on what is in the bioreactor, such as development media, water, or a salt solution. For instance, after early singulation, the s-frames with the separated and singulated immature embryos may be loaded into a bioreactor in the presence of a development medium for further development and maturation of the separated and singulated immature embryos. In another embodiment, after normal singulation, the s-frames with the separated and singulated mature embryos may be loaded into a bioreactor in the presence of water or a salt solution for conditioning the separated and singulated mature embryos.

As described above, the SSR system comprises a number of modules or processing stations. During operation of the SSR system, the s-frames move sequentially through the processing line from the dispensing module 100, the loading module 200, the spray module 300, and the drying module 400. The s-frames may be transferred from module to module through the system by use of the robotic arm 600.

As shown in FIGS. 2 and 3, the robotic arm 600 includes an arm 610, a connecting member 620, a base 630, and a motor (not shown) for driving the robotic arm 600. A downward opening 612 may be provided at the front end of the arm 610; the opening 612 may be used to hold the left or right side of the frame of an s-frame so as to move the s-frame from module to module. The arm 610 may be connected to the connecting member 620 which may be fixed on the base 630. The connecting member 620 may include a pneumatic cylinder (not shown) which can lower or raise the arm 610. The pneumatic cylinder allows the arm 610 to engage or disengage the s-frame. When the arm 610 is lowered, the opening 612 may engage the s-frame so as to move it to any predetermined positions. When the arm 610 is raised, the opening may disengage the s-frame so that the robotic arm 600 can travel freely up and down the processing line. The base 630 may be movably attached to a linear slide rail 650 to provide the range of motion necessary to cover the processing area encompassed by the modules 100, 200, 300, and 400 of the SSR system. The slide rail 650 may be positioned behind the processing line of the SSR system and fixed on the operation table. The maximum height of the robotic arm 600 needs to be a certain amount less than the height of the spray hood 350 raised by the lift mechanism 360 so that the robotic arm can freely move below the spay hood 350 when the spay hood 350 is raised by the lift mechanism 360.

By way of example and without limitation, during operation of the SSR system 10, the robotic arm 600 may be operable to transfer s-frames from module to module in a predetermined sequence. At any one time, a first s-frame may be positioned on the spray platform 310, a second s-frame may be positioned on the loading platform 410, and a third blank s-frame may be partially ejected from the dispensing module 100. The robotic arm 600 may be initially located at any suitable position between the loading module 200 and the spray module 300. Once the SSR system 10 is started by an operator, the robotic arm 600 may move to the leftmost end of the processing platform of the SSR system 10 and hold the right side of the third blank s-frame to pull it out from the s-frame canister 102 to the predetermined loading position at the loading module 200. Meanwhile, the second s-frame with loaded embryos and ESM may be pushed towards the predetermined spray position by the third blank s-frame pulled out by the robotic arm 600. The first s-frame with separated and singulated embryos after the spray process may be pushed towards the drying module 400 by the second s-frame. Then, the robotic arm 600 may adjust the second s-frame to the precise spray position. Next, the robotic arm 600 may hold the left side of a first s-frame with separated and singulated embryos and move it across the elongated opening 422 of the drying module 400 at a certain speed for drying the s-frame with separated and singulated embryos. The dried first s-frame may be manually transferred to the COW box 520 for conditioning developed embryos after normal singulation or transferred to any other suitable container for storing immature embryos after early singulation so as to clear the drying platform 410 for being prepared for next operation. When the first s-frame is entirely moved across the elongated opening 422, the robotic arm 600 may return to its initial position and be prepared for the next motion circle based on a control signal from a control device 700 as shown in FIG. 9.

In an embodiment, the robotic arm may be controlled to move given distances so as to transfer an s-frame to the predetermined loading position or the predetermined spray position, or move an s-frame across the drying module 400 at a given speed. Alternatively, there may be provided a plurality of position sensors along the loading platform 210, the spray platform 310, and the drying platform 410. The plurality of position sensors may be coupled to the control device 700. The control device 700 may control the motion of the robotic arm 600 based on signals from the plurality of position sensors.

Figure 9:
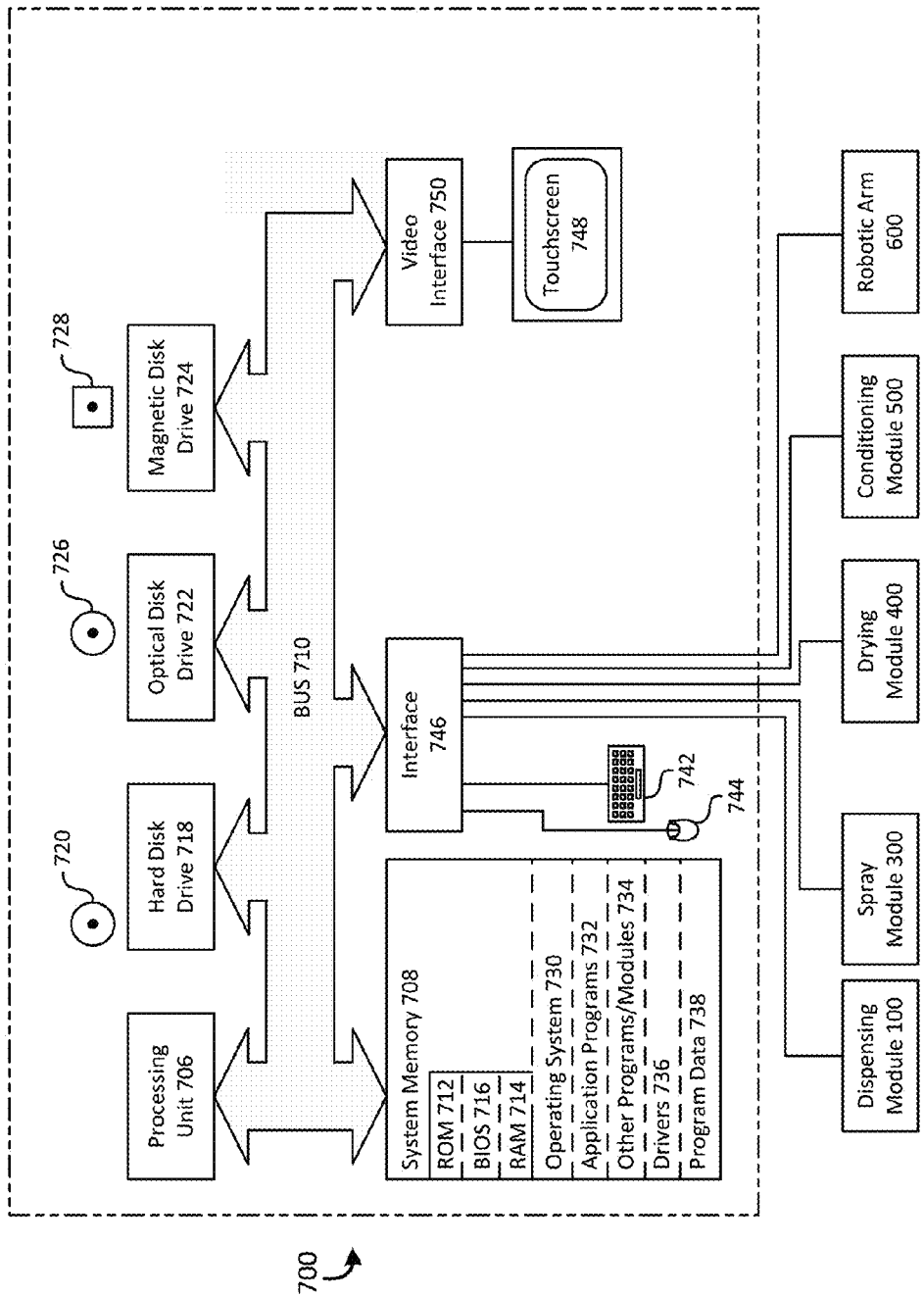
FIG. 9 is a schematic diagram of a control device for use in a SSR system.
Figure 10:
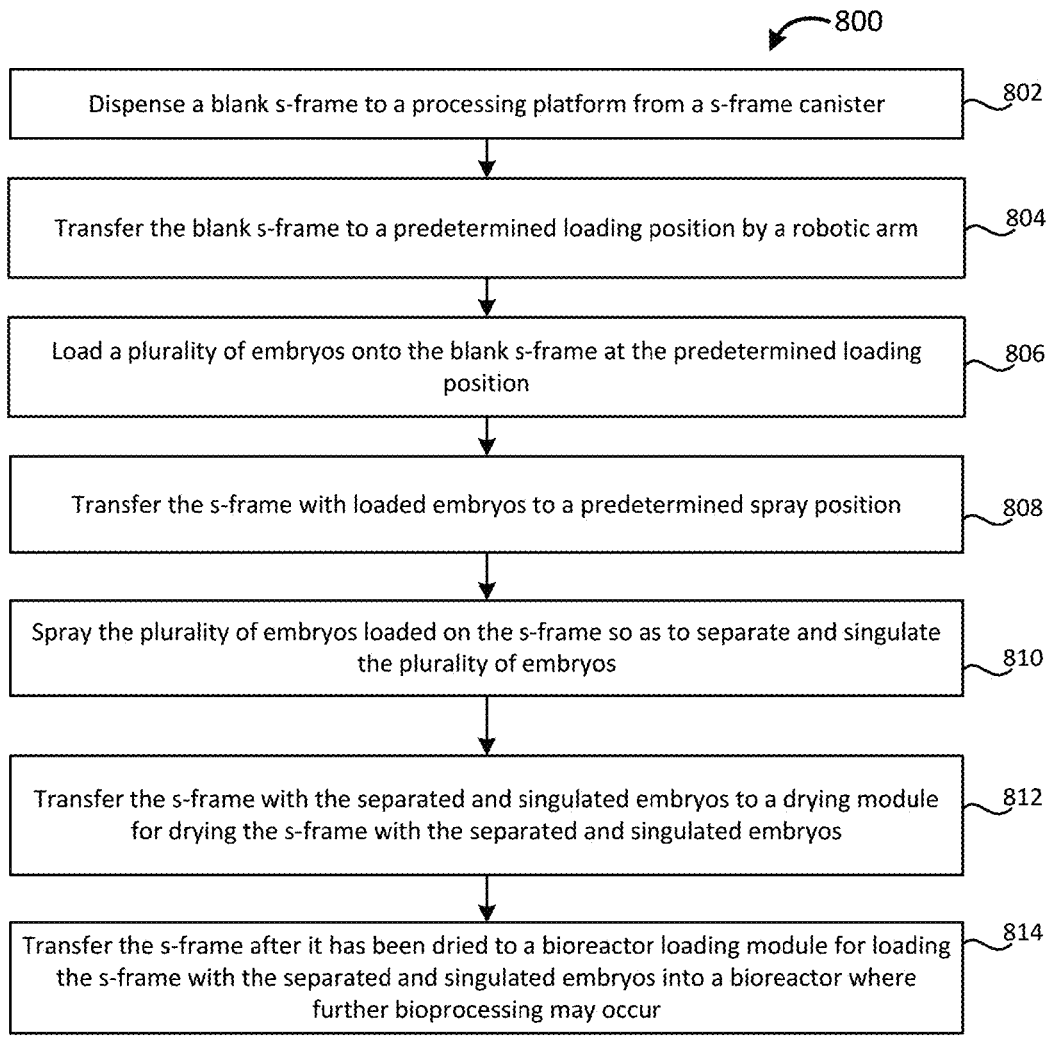
FIG. 10 is a flow diagram of a method of separating and singulating embryos according to one embodiment.

FIG. 9 illustrates one embodiment of the control device 700. As shown in FIG. 10, the control device 700 may be coupled to the dispensing module 100, the spray module 300, the drying module 400, the bioreactor loading module 500, and the robotic arm 600. The control device 700 may be used to control the ejection of s-frames at the dispensing module 100, control the lift mechanism 360 and spray time at the spray module 300, control the drying time at the drying module 400, and control the motion of the robotic arm 600 along the slide rail 650.

As shown in FIG. 9, the control device 700 includes a processing unit 706, a system memory 708, and a system bus 710 that couples various system components including the system memory 708 and the processing unit 706. The processing unit 706 may be any logic processing unit, such as one or more central processing units (CPUs), programmable logic controllers (PLC), distributed control system (DCS), and digital signal processors (DPS), etc. The system bus 710 can employ any known bus structures or architectures, including a memory bus with memory controller, a peripheral bus, and a local bus. The system memory 708 includes read-only memory ("ROM") 712 and random access memory ("RAM") 714. A basic input/output system ("BIOS") 716, which can form part of the ROM 712, contains basic routines that help transfer information between elements within the control device 700, such as during start-up.

The control device 700 may include a storage device, such as a hard disk drive 718 for reading from and writing to a hard disk 720, and an optical disk drive 722 and a magnetic disk drive 724 for reading from and writing to removable optical disks 726 and magnetic disks 728, respectively. The optical disks 726 can be a CD or a DVD, while the magnetic disk 728 can be a magnetic floppy disk or diskette. The hard disk drive 718, optical disk drive 722, and magnetic disk drive 724 may communicate with the processing unit 706 via the system bus 710. The drives 718, 722, 724, and their associated computer-readable media 720, 726, 728, may provide nonvolatile storage of computer-readable instructions, data structures, program modules and other data for the control device 700. Although the depicted control device 700 employs hard disk 720, optical disk 726, and magnetic disk 728, those skilled in the relevant art will appreciate that other types of computer-readable media that can store data and instruction accessible by a computer may be employed, such as magnetic cassettes, flash memory cards, Bernoulli cartridges, RAMs, ROMs, smart cards, etc. In other embodiments, the control device 700 need not include the drives 718, 722, 724, and their associated computer-readable media 720, 726, 728.

Program modules can be stored in the system memory 708, such as an operating system 730, one or more application programs 732, other programs or modules 734, drivers 736, and program data 738. While shown in FIG. 9 as being stored in the system memory 708, the operating system 730, one or more application programs 732, other programs or modules 734, drivers 736, and program data 738 can be stored on the hard disk 720 of the hard disk drive 218, the optical disk 726 of the optical disk drive 722 and/or the magnetic disk 728 of the magnetic disk drive 724. A user can enter commands and information into the control device 700 through input devices such as a keyboard 742 and/or a pointing device such as a mouse 744. These or other input devices may be connected to the processing unit 706 through an interface 746 such as a universal serial bus "USB" interface that couples to the system bus 710, although other interfaces such as a parallel port, a game port or a wireless interface or a serial port may be used. A touchscreen 748 or other display device may be coupled to the system bus 710 via a video interface 750, such as a video adapter. Although not shown, the control device 700 can include other output devices, such as speakers, printers, etc. In other embodiment, the control device 700 needs not include any display device and any output devices, such as speakers, printers, etc. Optionally, the control device 700 may include a start button 760 and a stop button 762 for starting and stopping the application programs stored in the system memory 708 so as to implement necessary automated control of the SSR system.

The SSR system of the disclosure can significantly improve germination of plant embryos. Compared to existing standard protocol (e.g., hand transfers of embryos), the SSR system may improve germination of plant embryos by about 5% to about 7%.

FIG. 10 shows a method 800 of separating and singulating embryos by using the SSR system.

At 802, an s-frame may be at least partially ejected to a processing platform from an s-frame canister at a dispensing module of a SSR system. The s-frame may comprise a frame and a porous substrate which may be mounted in the frame and comprise a plurality of pores. The diameters of the pores may be referred to the opening width. The pore opening width may be in the range of from about 500 microns to about 2000 microns, such as about 810 micron for normal singulation and about 700 micron for early singulation. The ratio of open area formed by all pores to the total area of the porous substrate may be referred to as open area percentage. By way of example and without limitation, the open area percentage may be equal to or greater than 50%, preferably equal to or greater than 55%.

At 804, the porous substrate may be transferred by a robotic arm to a predetermined loading position at a loading module At 806, a plurality of embryos may be loaded onto the top surface of the porous substrate at the predetermined loading position.

At 808, the porous substrate with loaded embryos may be transferred by the robotic arm to a predetermined spray position at a spray module.

At 810, when the porous substrate with disposed embryos is located at the predetermined spray position, a spray hood may be lowered to engage around the frame of the s-frame to form a seal, thereby creating a closed spray environment. A spray nozzle adjustably mounted at the approximate center of the internal top surface of the spray hood may be configured to discharge a spray pattern designed to separate desired embryos from the underlying ESM and undersized embryos by pushing ESM and undersized embryos through the pores of the porous substrate and singulate desired embryos retained on the s-frame by scattering them on the top surface of the porous substrate of the s-frame. The spray distance between the spray nozzle and the top surface of the porous substrate may be adjustable by raising or lowering the spray nozzle. The spray angle of the spray module may range from about 25 degrees to about 35 degrees, such as from about 26 degrees to about 32 degrees. The spray pressure at the spray nozzle 320 may range from 20 to 50 psi, preferably approximately 30 psi. The spray time may range from 2 to 30 second, such as 20 seconds for normal separation and 4 seconds for early separation. When the spray process is finished, the spray hood may be lifted by a lift mechanism. The s-frame with separated and singulated embryos may be transferred by the robotic arm to a drying module At 812, after spray separation and singulation at the spray module, the porous substrate with separated and singulated embryos may be transferred by the robotic arm to a drying module. The porous substrate with separated and singulated embryos may be moved by the robotic arm at a certain speed across an elongated opening of a vacuum housing located between the first section and the second section of a drying platform, whereby the bottom surface of the porous substrate of the s-frame being in contact with the elongated opening which is in communication with a vacuum source, results in spray liquid being removed from the s-frame and air being drawn over and around the embryos disposed on the top surface of the porous substrate and through the porous substrate. The dispensing module, the loading module, the spray module, the drying module may be arranged consecutively in a line from left to right or from right to left so that the porous substrate can be linearly transferred from one end to the other end of a processing line of the SSR system. The porous substrate may be transferred by the robotic arm from module to module in a predetermined sequence. Optionally, the SSR system may include two processing lines which are arranged opposite to each other.

At 814, after drying at the drying module, the s-frame with separated and singulated embryos may be transferred to a bioreactor loading module for loading the s-frame upon which the separated and singulated embryos are retained into a bioreactor where further bioprocessing may occur. The further bioprocessing may be further development, maturation, or conditioning depending on the stage of embryos. The further bioprocessing may also depend on what is in the bioreactor, such as development media, water, or a salt solution. For instance, after early singulation, the s-frames with the separated and singulated immature embryos may be loaded into a bioreactor in the presence of a development medium for further development and maturation of the separated and singulated immature embryos. In another embodiment, after normal singulation, the s-frames with the separated and singulated mature embryos may be loaded into a bioreactor in the presence of water or a salt solution for conditioning the separated and singulated mature embryos.

Optionally, the method 800 of separating and singulating embryos by using the SSR system may comprise a step of counting or at least estimating the number of separated and singulated embryos by an overhead vision mechanism. The overhead vision mechanism may be centered over the porous substrate after it has been dried at the drying module. The overhead vision mechanism may comprises an image generator for capturing the image of the separated and singulated embryos retained on the porous substrate and a light source for illuminating the separated and singulated embryos retained on the porous substrate. The light source may be positioned such that a beam of light produced by the light source is approximately centered about the center of the porous substrate after it has been dried at the drying module.

The various features and processes described above may be used independently of one another, or may be combined in various ways. All possible combinations and sub-combinations are intended to fall within the scope of this disclosure. In addition, certain method or process steps or blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While certain example embodiments have been described, these embodiments have been presented by way of example only, and are not intended to limit the scope of the disclosures herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions and changes in the form of the methods and systems described herein may be made without departing from the spirit of the disclosures herein. The accompanying claims and their equivalents are intended to cover such forms or modifications as would fall within the scope and spirit of certain of the disclosures herein.

What is claimed:

1. A system for separating and singulating embryos, comprising:
    a dispensing module configured to dispense a blank porous substrate mounted in a frame;
    a loading module for loading a plurality of embryos onto the porous substrate;
    a spray module configured to spray a plurality of embryos loaded on the porous substrate so as to separate and singulate the plurality of embryos;
    a drying module configured to dry the porous substrate upon which the plurality of separated and singulated embryos are retained;
    a bioreactor loading module configured for loading the porous substrate upon which the plurality of separated and singulated embryos are retained into a bioreactor; and
    a robotic arm operable to transfer the porous substrate from the spray module to the drying module;
    wherein the dispensing module, the loading module, the spray module, the drying module, and the bioreactor loading module are arranged consecutively in a line from left to right or from right to left so that the porous substrate can be linearly transferred from one end to the other end of a processing line.

2. The system of claim 1 wherein the spray module comprises:
    a spray hood capable of being raised or lowered by a lift mechanism and capable of engaging around a frame in which the porous substrate is mounted to create an isolated spray environment when lowered; and
    a spray nozzle mounted to the approximate center of the internal top surface of the spray hood.

3. The system of claim 2 wherein the spray distance between the spray nozzle and the top surface of the porous substrate is adjustable by raising or lowering the spray nozzle.

4. The system of claim 2 wherein the spray angle of the spray nozzle is in the range of from about 26 degrees to about 32 degrees.

5. The system of claim 2 wherein the spray pressure at the spray nozzle is in the range of from about 20 psi to about 50 psi.

6. The system of claim 2 wherein the spray time of the spray module is in the range of from about 2 to about 30 seconds.

7. The system of claim 1 wherein the porous substrate comprises a plurality of pores, each of the plurality of pores having an opening width of from about 500 microns to about 2000 microns.

8. The system of claim 7 wherein the open area percentage of the porous substrate is equal to or greater than about 55%.

9. The system of claim 1 wherein the system comprises two processing lines which are arranged opposite to each other.

10. The system of claim 1, further comprising a control device configured to control the operation of the system, the control device being coupled to the dispensing module, the spray module, the drying module, the bioreactor loading module, and the robotic arm.

11. The system of claim 1, further comprising an overhead vision mechanism configured to count or at least estimate the number of separated and singulated embryos, the overhead vision mechanism being centered over the porous substrate after it has been dried at the drying module.

12. The system of claim 11 wherein the overhead vision mechanism comprises:
    an image generator configured to capture the image of the separated and singulated embryos retained on the porous substrate; and
    a light source configured to illuminate the separated and singulated embryos retained on the porous substrate, the light source being positioned such that a beam of light produced by the light source is approximately centered about the center of the porous substrate after it has been dried at the drying module.

13. A method of separating and singulating embryos, comprising:
    dispensing a blank porous substrate mounted in a frame from a dispensing module;
    loading a plurality of embryos onto the blank porous substrate while it is transferred to a predetermined loading position at a loading module;
    spraying the plurality of embryos loaded on the porous substrate so as to separate and singulate the plurality of embryos at a spray module;
    transferring the porous substrate from the spray module to a drying module; and drying the porous substrate upon which the plurality of separated and singulated embryos are retained at the drying module; and loading the porous substrate upon which the plurality of separated and singulated embryos are retained into a bioreactor at a bioreactor loading module;

wherein the dispensing module, the loading module, the spray module, the drying module, and the bioreactor loading module are arranged consecutively in a line from left to right or from right to left so that the porous substrate can be linearly transferred from one end to the other end of a processing line.

14. The method of claim 13 wherein the spray module comprises:

a spray hood configured to be raised or lowered by a lift mechanism and engage around a frame in which the porous substrate is mounted to create a closed spray environment when lowered; and a spray nozzle mounted to the approximate center of the internal top surface of the spray hood.

15. The method of claim 14 wherein the spray distance between the spray nozzle and the top surface of the porous substrate is adjustable by raising or lowering the spray nozzle.

16. The method of claim 14 wherein the spray angle of the spray nozzle is in the range of from about 26 degrees to about 32 degrees.

17. The method of claim 14 wherein the spray pressure at the spray nozzle is in the range of from about 20 psi to about 50 psi.

18. The method of claim 14 wherein the spray time of the spray module is in the range of from about 2 to about 30 seconds.

19. The method of claim 14 wherein the porous substrate comprises a plurality of pores, each of the plurality of pores having an opening width of from about 500 microns to about 2000 microns.

20. The method of claim 19 wherein the open area percentage of the porous substrate is equal to or greater than about 55%.

21. The method of claim 13 wherein two processing lines are arranged opposite to each other.

22. The method of claim 13, further comprising controlling the operation of the processing line by a control device.

23. The method of claim 22, further comprising counting or at least estimating the number of separated and singulated embryos by an overhead vision mechanism, the overhead vision mechanism being centered over the porous substrate after it has been dried at the drying module.

24. The method of claim 23 wherein the overhead vision mechanism comprises:

an image generator configured to capture the image of the separated and singulated embryos retained on the porous substrate; and a light source configured to illuminate the separated and singulated embryos retained on the porous substrate, the light source being positioned such that a beam of light produced by the light source is approximately centered about the center of the porous substrate after it has been dried at the drying module.

25. A system for separating and singulating embryos, comprising:

a spray module configured to spray a plurality of embryos loaded on a porous substrate so as to separate and singulate the plurality of embryos;

a drying module configured to dry the porous substrate upon which the plurality of separated and singulated embryos are retained;

an overhead vision mechanism configured to count or at least estimate the number of separated and singulated embryos, the overhead vision mechanism being centered over the porous substrate after it has been dried at the drying module; and a robotic arm operable to transfer the porous substrate from the spray module to the drying module.

26. The system of claim 25 wherein the overhead vision mechanism comprises:

an image generator configured to capture the image of the separated and singulated embryos retained on the porous substrate; and a light source configured to illuminate the separated and singulated embryos retained on the porous substrate, the light source being positioned such that a beam of light produced by the light source is approximately centered about the center of the porous substrate after it has been dried at the drying module.

27. A method of separating and singulating embryos, comprising:

spraying a plurality of embryos loaded on a porous substrate so as to separate and singulate the plurality of embryos at a spray module;

transferring the porous substrate from the spray module to a drying module; and drying the porous substrate upon which the plurality of separated and singulated embryos are retained at the drying module; and counting or at least estimating the number of separated and singulated embryos by an overhead vision mechanism, the overhead vision mechanism being centered over the porous substrate after it has been dried at the drying module.

28. The method of claim 27 wherein the overhead vision mechanism comprises:

an image generator configured to capture the image of the separated and singulated embryos retained on the porous substrate; and a light source configured to illuminate the separated and singulated embryos retained on the porous substrate, the light source being positioned such that a beam of light produced by the light source is approximately centered about the center of the porous substrate after it has been dried at the drying module.

* * * * *

UNITED STATES PATENT AND TRADEMARK OFFICE
CERTIFICATE OF CORRECTION

| | | |
|---|---|---|
| PATENT NO. | : 9,688,953 B2 | Page 1 of 1 |
| APPLICATION NO. | : 14/665344 | |
| DATED | : June 27, 2017 | |
| INVENTOR(S) | : Anthony P. Swanda et al. | |

It is certified that error appears in the above-identified patent and that said Letters Patent is hereby corrected as shown below:

In the Specification

In Column 5, Line 35, delete "251 F)." and insert -- 251 °F). --, therefor.

In Column 13, Line 39, after "module" insert -- . --.

In Column 14, Line 3, after "module" insert -- . --.

Signed and Sealed this
Third Day of October, 2017

Joseph Matal
*Performing the Functions and Duties of the*
*Under Secretary of Commerce for Intellectual Property and*
*Director of the United States Patent and Trademark Office*